US009128074B2

(12) United States Patent
Han et al.

(10) Patent No.: US 9,128,074 B2
(45) Date of Patent: Sep. 8, 2015

(54) DETECTION METHOD USING COLORIMETRIC ANALYSIS (75) Inventors: ChangSoo Han, Daejeon (KR); Duck Jong Kim, Daejeon (KR); Tripathy Suraj Kumar, Daejeon (KR)

(73) Assignee: Korean Institute of Machinery & Materials, Yuseong-Gu, Daejeon (KR)

(*) Notice: Subject to any disclaimer, the term of this patent is extended or adjusted under 35 U.S.C. 154(b) by 0 days.

(21) Appl. No.: 13/581,850

(22) PCT Filed: Apr. 2, 2012

(86) PCT No.: PCT/KR2012/002473
§ 371 (c)(1),
(2), (4) Date: Aug. 30, 2012

(87) PCT Pub. No.: WO2013/032095
PCT Pub. Date: Mar. 7, 2013

(65) Prior Publication Data
US 2014/0199773 A1 Jul. 17, 2014

(30) Foreign Application Priority Data
Aug. 30, 2011 (KR) .................. 10-2011-0086881

(51) Int. Cl.
G01N 33/00 (2006.01)
G01N 33/18 (2006.01)
G01N 21/00 (2006.01)
G01N 31/22 (2006.01)
G01N 21/78 (2006.01)

(52) U.S. Cl.
CPC ............ G01N 33/182 (2013.01); G01N 21/78 (2013.01); G01N 31/22 (2013.01); G01N 33/18 (2013.01); Y10T 436/12 (2015.01); Y10T 436/153333 (2015.01); Y10T 436/193333 (2015.01)

(58) Field of Classification Search
CPC ....... G01N 21/00; G01N 33/00; G01N 33/18; G01N 31/221; G01N 31/22; G01N 31/00; Y10T 436/15; Y10T 436/19; Y10T 436/153333; Y10T 436/193333; Y10T 436/12; Y10T 436/00
USPC .................................. 436/101, 100
See application file for complete search history.

(56) References Cited

U.S. PATENT DOCUMENTS

| 6,143,572 | A | 11/2000 | Grand |
| 7,808,632 | B2 | 10/2010 | Vaidya |
| 2004/0132217 | A1 | 7/2004 | Prince |
| 2005/0009194 | A1 | 1/2005 | Franklin |
| 2007/0031972 | A1 | 2/2007 | Attar |
| 2008/0306230 | A1* | 12/2008 | Pan et al. ................. 526/171 |
| 2008/0318249 | A1 | 12/2008 | Powell |
| 2010/0068817 | A1 | 3/2010 | Mirkin |
| 2011/0171749 | A1* | 7/2011 | Alocilja et al. ........... 436/501 |
| 2011/0207232 | A1 | 8/2011 | Ostafin |

FOREIGN PATENT DOCUMENTS

| CN | 101261220 A | * 9/2008 | ............ G01N 21/33 |
| EP | 1462528 | 9/2004 | |
| JP | 1999-281569 | 10/1999 | |
| JP | 2004-181284 | 7/2004 | |
| JP | 2004-184084 | 7/2004 | |
| JP | 2007-196175 | 8/2007 | |
| JP | 2007-303997 | 11/2007 | |
| JP | 2008-039692 | 2/2008 | |
| JP | 2009-122077 | 6/2009 | |
| JP | 2009-204554 | 9/2009 | |
| KR | 10-0223822 | 7/1999 | |
| KR | 10-0729668 | 6/2007 | |
| KR | 10-0787046 | 12/2007 | |
| KR | 10-2009-0092907 | 9/2009 | |
| KR | 10-0947262 | 9/2009 | |
| KR | 10-2010-0034816 | 4/2010 | |
| KR | 10-0958184 | 5/2010 | |
| KR | 10-0963540 | 6/2010 | |
| KR | 10-2011-0014819 | 2/2011 | |

OTHER PUBLICATIONS

Hui et al, Machine Translation of Description of CN 101261220A, Detection of single chain DNA base mutation for clinical application comprises utilization of gold nanoparticles in DNA mixture during UV visible spectrum detection, obtained on Oct. 28, 2014, pp. 1-7.*
Yong Hwa Do et al., Detection of Methanol concentration using SPR, Proceedings of the Optical Society of Korea Annual Meeting, Feb. 15-16, 2001, Korea.
Eun Jung Sin et al., A portable surface plasmon resonance sensor system for detection ofC-reactive protein using SAM with dimer structure, J. of the Korean Sensors Society, 2010, pp. 456-461,vol. 19, No. 6, Korea.
Y.J. Cho et al., Measurement of Alcohol Contents in Alcoholic Beverages Using a Surface Plasmon Resonance Sensor, J. of Biosysems Engineering, 2004, pp. 323-328,vol. 29, No. 4, Korea.
Yong Hwa Do et al., Analysis of ethanol concentration and refractive-index by use of surface plasmon resonance effect, Hankook Kwanghak Hoeji, Feb. 2002, vol. 13, No. 1, Korea.
Amir Reza Sadrolhosseini et al., Surface Plasmon Resonance Determination of Methanol Concentration During Alkaline Transestrification, APRN Journal of Engineering and Applied Sciences, Sep. 2010, vol. 5, No. 9.

(Continued)

Primary Examiner — Christine T Mui
(74) Attorney, Agent, or Firm — Fox Rothschild LLP/D. Monin (57) ABSTRACT A detection method using colorimetric analysis of the present invention includes: providing a first solution in which two materials selected from metal nanoparticles, an oxidizing agent, and chloride ions are mixed; providing a second solution including one other material that is not included in the first solution among the metal nanoparticles, the oxidizing agent, and the chloride ions; preparing a mixture solution by mixing the first solution and the second solution; and testing and measuring a color change of the mixture solution.

9 Claims, 11 Drawing Sheets

(56) References Cited

OTHER PUBLICATIONS

Suraj Kumar Tripathy et al., Highly Selective Colorimetric Detection of Hydrochloric Acid Using Unlabeled Gold Nanoparticles and an Oxidizing Agent, Analytical Chemistry, School of Mechanical Engineering, Korea University, Seoul, Korea, Anal. Chem. 2011, 83, pp. 9206-8212.

Korean Intellectual Property Office, International Search Report, PCT/KR2012/002473, Oct. 16, 2012.

European Search Report issued Jul. 17, 2015 in Application No. PCT/KR2012/002473 (English translation).

Shu-Pao Wu et al: "Colorimetric detection of $Fe^{3+}$ ions using pyrophosphate functionalized gold nanoparticles", The Analyst, vol. 136, No. 9, Mar. 4, 2011 p. 1887-1891, XP055198320, ISSN: 0003-2654, DOI: 10.1039/c1an15028f.

\* cited by examiner

DETECTION METHOD USING COLORIMETRIC ANALYSIS

CROSS-REFERENCE TO RELATED APPLICATION

This application is a National Stage application of PCT/KR2011/002473 filed on Apr. 2, 2012, which claims priority to Korean Patent Application No. 10-2011-0086881 filed on Aug. 30, 2011, the entire contents of which are hereby incorporated by reference.

TECHNICAL FIELD

The present invention relates to a detection method using a characteristic that a color is changed under mixing.

BACKGROUND ART

Currently, water pollution has become one of the most challenging issues for mankind, and rapid industrialization has lead to increase in the release of toxic chemicals into the natural water systems.

Chlorine containing inorganic acids in general and hydrochloric acid (HCl) in particular are among the biggest contributor of water pollution. Because of its extensive applications, excellent stability and mobile nature in aqueous environments, hydrochloric acid (HCl) is a potent acidifier of wetlands, and water resources. In addition to illegal dumping of wastes from various industries, the accidental leakage has raised concern among the environmentalists.

However, any rapid and selective detection technique is not yet developed.

The above information disclosed in this Background section is only for enhancement of understanding of the background of the invention and therefore it may contain information that does not form the prior art that is already known in this country to a person of ordinary skill in the art.

DISCLOSURE OF INVENTION

Technical Problem

The present invention provides a detection method detecting hydrochloric acid (chloride ions) in aqueous environment by using colorimetric, label-free, and non-aggregation-based metal nanoparticles probe.

Also, the present invention provides an oxidizing agent detection method using a metal nanoparticle test, or a detection method detecting an oxidizing agent or hydrochloric acid (chloride ions).

Solution to Problem

A detection method using colorimetric analysis according to an exemplary embodiment of the present invention includes: providing a first solution in which two materials selected from metal nanoparticles, an oxidizing agent, and chloride ions are mixed; providing a second solution including one other material that is not included in the first solution among the metal nanoparticles, the oxidizing agent, and the chloride ions; preparing a mixture solution by mixing the first solution and the second solution; and testing and measuring color change of the mixture solution.

As another exemplary embodiment, the first solution may be provided as a detection solution in which the metal nanoparticles and the oxidizing agent are mixed, the second solution may be provided as a detection target including the chloride ions, and the detection solution may be mixed with the detection target to test and measure the color change, thereby testing and detecting the chloride ions of the detection target.

The detection target may include at least one among sea water, stream water, pond water, tap water, and deionized water including the chloride ions. The detection target including the chloride ions may be hydrochloric acid Also, as another exemplary embodiment, the first solution may be provided as the detection solution in which the metal nanoparticles and the chloride ions are mixed, the second solution may be provided as the detection target including the oxidizing agent, the detection solution may be mixed with the detection target, and the color change may be tested and measured, thereby testing and detecting the oxidizing agent of the detection target.

As another exemplary embodiment, the first solution may be provided as the detection solution in which the oxidizing agent and the chloride ions are mixed, the second solution may be provided as the detection target including the metal nanoparticles, the detection solution may be mixed with the detection target, and the color change may be tested and measured, thereby testing and detecting the metal nanoparticles of the detection target.

The diameter of the metal nanoparticles may be in a range of 10 to 100 nm, and preferably in range of 20 to 30 nm.

The metal nanoparticles may include at least one of gold (Au) nanoparticles and silver (Ag) nanoparticles.

The oxidizing agent may include at least one of nitric acid ($HNO_3$) and hydrogen peroxide ($H_2O_2$).

In the testing and measuring of the color change of the mixture solution, after the detection solution and the detection target are mixed and left for a predetermined time, the color change may be tested and measured by comparing with the detection target before the mixing.

Advantageous Effects of Invention

According to an exemplary embodiment of the present invention, a selective recognition technique of hydrochloric acid in a water environment based on hydrochloric acid dissolution caused by an absorption reduction of gold nanoparticles is possible. The process according to an exemplary embodiment of the present invention does not use any leveling agent such that the process is simple and easy to use.

This process has high separation sensitivity from the common salts and the negative ions may be directly used in a natural number system. Through these characteristics, the system according to the present invention may be a possible means for testing of hydrochloric acid in a sea ecosystem that is easily exposed to industrial pollution.

MODE FOR THE INVENTION

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention. The drawings and description are to be regarded as illustrative in nature and not restrictive. Like reference numerals designate like elements throughout the specification.

Figure 1:
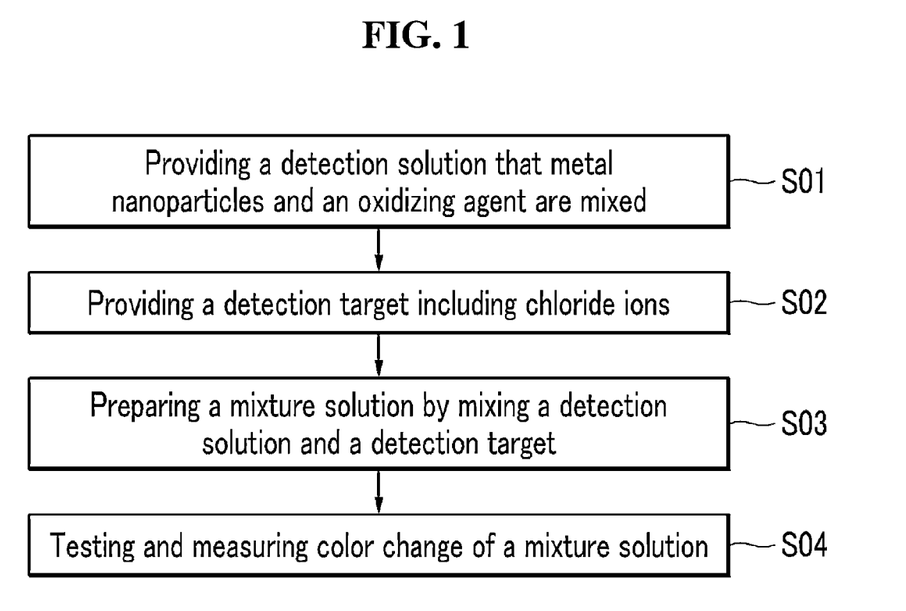
FIG. 1 is a flowchart of a chloride ion detection method according to the first exemplary embodiment of the present invention.

FIG. 1 is a flowchart of a chloride ion detection method according to the first exemplary embodiment of the present invention. Referring to FIG. 1, a chloride ion detection method according to the present exemplary embodiment will be described.

Firstly, a detection solution mixed with metal nanoparticles and an oxidizing agent is provided (S01). A diameter of the metal nanoparticles may be formed to be in a range of 10 to 100 nm, and preferably in the range of 20 to 30 nm. The metal nanoparticles may include gold (Au) nanoparticles or silver (Ag) nanoparticles.

The oxidizing agent may be a strong oxidizing agent, for example, nitric acid ($HNO_3$) or hydrogen peroxide ($H_2O_2$).

Next, a detection target including chloride ions ($Cl^-$) is provided (S02).

The detection target may exist with an aqueous solution in which hydrogen chloride (HCl) is dispersed, that is, a state of hydrochloric acid (HCl acid). Also, the detection target may include sea water, stream water, pond water, tap water, or deionized water including chloride ions ($Cl^-$).

Next, a mixture solution mixed with the detection solution and the detection target is prepared (S03). Before preparing the mixture solution, the color of the detection solution and the detection target is previously confirmed, thereby using the color as a comparison reference when a color change is generated after the reaction.

Then, the color change of the mixture solution is tested and measured (S04).

If the detection solution is injected to be mixed with the detection target including the chloride ions and is left for a predetermined time, the metal nanoparticles included in the detection solution and hydrogen ions ($H^+$) and chloride ions ($Cl^-$) react with the strong oxidizing agent included in the detection target, thereby generating chloride metal ions. At this time, a color change is generated in the mixture solution compared with the detection target before the mixture, and the speed of the color change may have a difference according to the concentration of hydrochloric acid.

Accordingly, a reference indicator is determined by previously confirming the reference color according to the concentration of the detection target, thereby also measuring a schematic concentration according to the color represented in the test.

Figure 2:
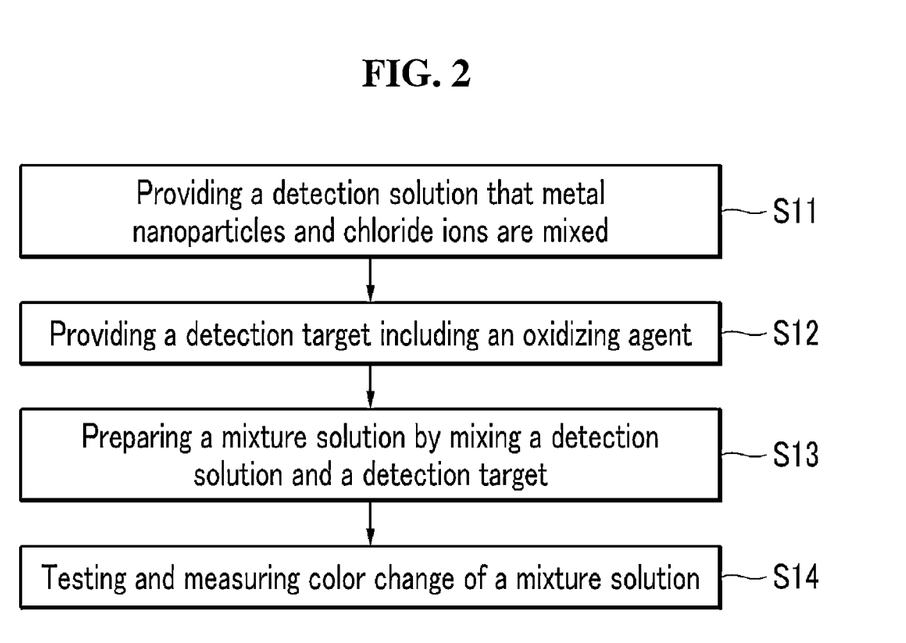
FIG. 2 is a flowchart of an oxidizing agent detection method according to the second exemplary embodiment of the present invention.

FIG. 2 is a flowchart of an oxidizing agent detection method according to the second exemplary embodiment of the present invention. Referring to FIG. 2, the oxidizing agent detection method according to the present exemplary embodiment will be described.

Firstly, a detection solution mixed with the metal nanoparticles and chloride ions ($Cl^-$) is provided (S11). A diameter of the metal nanoparticles may be in a range of 10 to 100 nm, and preferably in the range of 20 to 30 nm. The metal nanoparticles may selectively include gold (Au) nanoparticles or silver (Ag) nanoparticles. The detection solution may exist with an aqueous solution in which hydrogen chloride (HCl) is dispersed, that is, a state of hydrochloric acid (HCl acid).

Next, a detection target including an oxidizing agent is provided (S12).

The oxidizing agent may be a strong oxidizing agent, for example nitric acid ($HNO_3$) or hydrogen peroxide ($H_2O_2$).

Next, a mixture solution mixed with the detection solution and the detection target is prepared (S13). Before preparing the mixture solution, the color of the detection solution and the detection target is previously confirmed, thereby using the color as a comparison reference when a color change is generated after the reaction.

Then, the color change of the mixture solution is tested and measured (S14).

If the detection solution is injected to be mixed with the detection target including the oxidizing agent and is left for a predetermined time, the metal nanoparticles included in the detection solution and hydrogen ions ($H^+$) and chloride ions ($Cl^-$) included in the detection target react with the strong oxidizing agent, thereby generating chloride metal ions. At this time, a color change is generated in the mixture solution compared with the detection target before the mixture, and the speed of the color change may be different according to the concentration of hydrochloric acid.

Accordingly, a reference indicator is determined by previously confirming the reference color according to the concentration of the detection target, thereby measuring a schematic concentration according to the color represented in the test.

Figure 3:
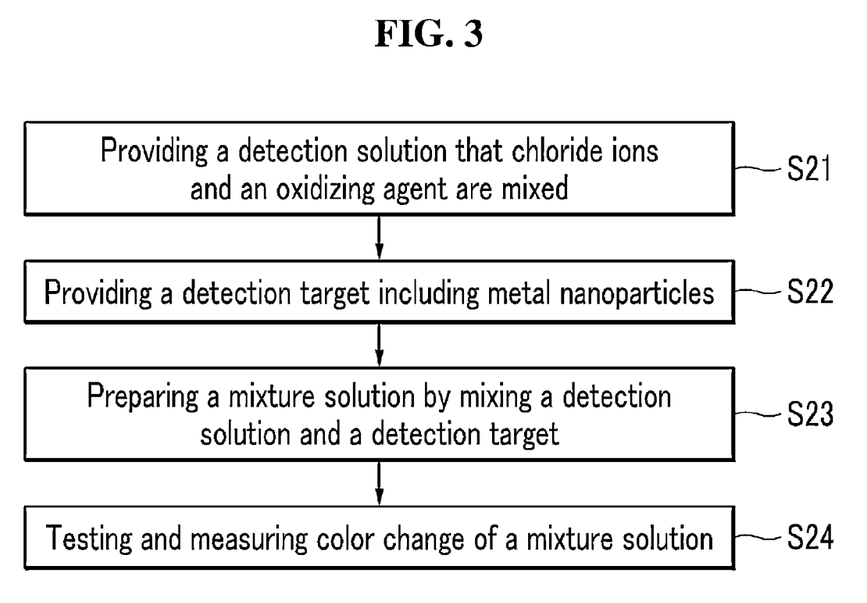
FIG. 3 is a flowchart of a metal nanoparticle detection method according to the third exemplary embodiment of the present invention.

FIG. 3 is a flowchart of a metal nanoparticle detection method according to the third exemplary embodiment of the present invention. Referring to FIG. 3, a metal nanoparticle detection method according to the present exemplary embodiment will be described.

Firstly, a detection solution mixed with the oxidizing agent and chloride ions (Cl⁻) is provided (S21). The detection solution may exist with an aqueous solution in which hydrogen chloride (HCl) is dispersed, that is, a state of hydrochloric acid (HCl acid). The oxidizing agent may be a strong oxidizing agent, for example nitric acid ($HNO_3$) or hydrogen peroxide ($H_2O_2$).

Next, the detection target including the metal nanoparticles is provided (S22).

The diameter of the metal nanoparticles may be in a range of 10 to 100 nm, and preferably in a range of 20 to 30 nm. The metal nanoparticles may selectively include gold (Au) nanoparticles or silver (Ag) nanoparticles.

Next, a mixture solution of the detection solution and the detection target is prepared (S23). Before preparing the mixture solution, the color of the detection solution and the detection target is previously confirmed, thereby using the color as a comparison reference when a color change is generated after the reaction.

Then, the color change of the mixture solution is tested and measured (S14).

If the detection solution is injected to be mixed with the detection target including the metal nanoparticles and is left for a predetermined time, the metal nanoparticles included in the detection target and hydrogen ions (H⁺) and chloride ions (Cl⁻) included in the detection solution react with the strong oxidizing agent, thereby generating chloride metal ions. At this time, a color change is generated in the mixture solution compared with the detection target before the mixture, and the speed of the color change may be different according to the concentration of hydrochloric acid.

Accordingly, a reference indicator is determined by previously confirming the reference color according to the concentration of the detection target, thereby also measuring a schematic concentration according to the color represented in the test.

Next, a detection mechanism using a color change as a case in which gold nanoparticles (Au NPs) and nitric acid ($HNO_3$) or hydrogen peroxide ($H_2O_2$) are mixed to use as a detection solution will be described.

A basic phenomenon of the detection is to leach gold nanoparticles (Au NPs) by an aqueous chloro-species in an environment including the strong oxidizing agent such as nitric acid or hydrogen peroxide. This process causes a remarkable reduction of a surface plasmon resonance (SPR) peak of a scattering of gold nanoparticles (Au NPs).

This technique depends on the size of the gold nanoparticles (Au NPs), and provides selectivity of a high degree between a mineral acid, a salt, and negative ions (anions) of a wide range. As described above, a simple and low cost probe may detect hydrochloric acid up to 500 ppm lower than a dangerous value in a natural water system.

Figure 4:
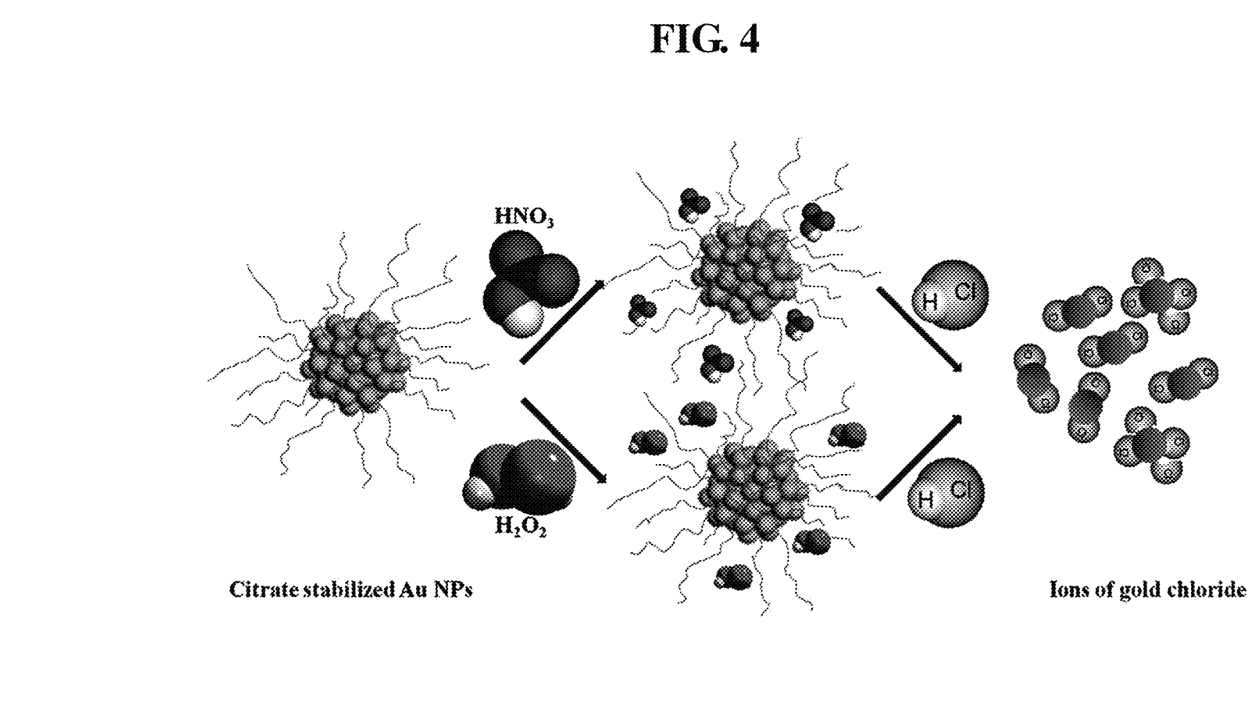
FIG. 4 is a schematic view showing a reaction in which gold (Au) nanoparticles are leached by hydrochloric acid in an environment including an oxidizing agent.

FIG. 4 is a schematic view showing a reaction in which gold (Au) nanoparticles (Au NPs) are leached by hydrochloric acid in an environment including an oxidizing agent. That is, a reaction generated between gold nanoparticles (Au NPs) and hydrochloric acid in the environment in which the strong oxidizing agent such as nitric acid ($HNO_3$) or hydrogen peroxide ($H_2O_2$) exists is diagramed.

The gold as a noble metal is not dissolved by a strong acid or a strong alkali. However, when the strong oxidizing agent and chloride ions exist together, the gold may be dissolved into a gold chloride species, that is $[Au(Cl)_2]^-$ or $[Au(Cl)_4]^-$, as in Chemical Formula 1.

$$Au^0(aq.) + nH^+ + nCl^- \xrightarrow{Oxidizing\ agent} [AuCl_x]^-$$ [Chemical Formula 1]

Here, x may be 2 or 4 depending upon the concentration of chloride ions, pH, and nature of the oxidizing agent.

Figure 5A:
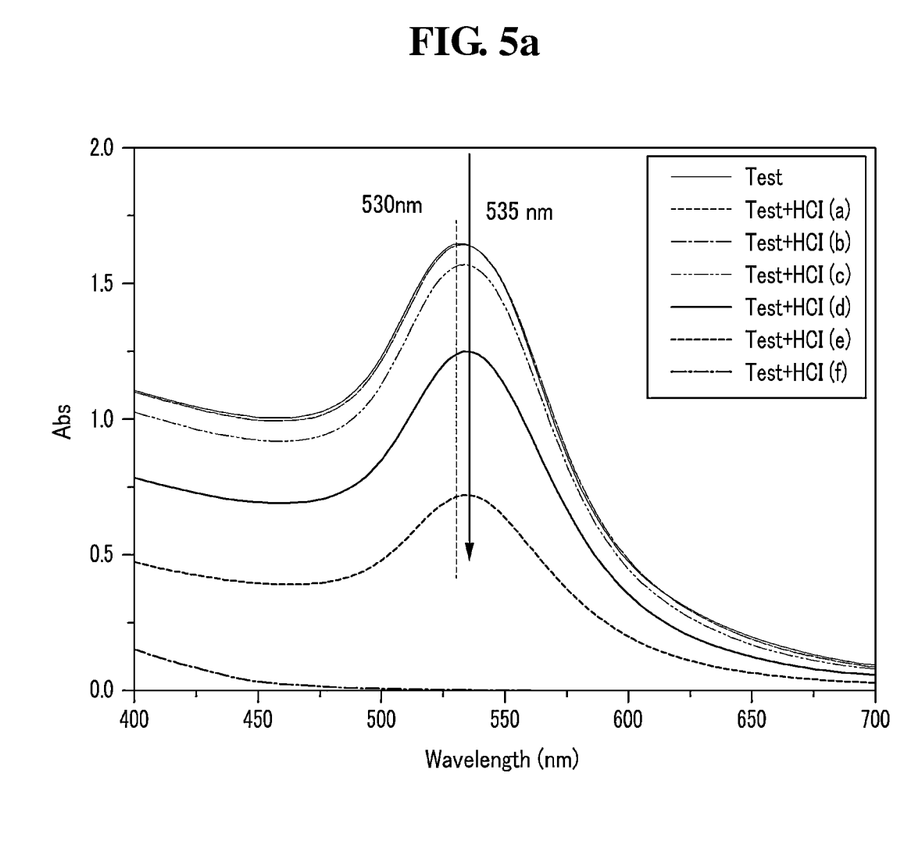
FIG. 5a is a view showing an ultraviolet ray-visible ray absorption spectrum of an gold nanoparticle aqueous dispersion using nitric acid as an oxidizing agent in an environment including hydrochloric acid of different concentrations.

FIG. 5a is a view showing an ultraviolet rays-visible ray absorption spectrum of a gold nanoparticle (Au NP) aqueous dispersion using nitric acid as an oxidizing agent in an environment including hydrochloric acid of different concentrations. The hydrochloric acid concentration of each graph is (a) 100 ppm, (b) 200 ppm, (c) 500 ppm, (d) 1,000 ppm, (e) 2,000 ppm, and (f) 5,000 ppm.

As shown in FIG. 5a, the gold nanoparticle aqueous dispersion has a remarkable absorption peak at 530 nm because of the surface plasmon resonance. The addition of the hydrochloric acid causes a result that the intensity of the absorption peak is quickly decreased in the ultraviolet rays-visible ray absorption spectrum. The absorption peak also has a red shift from 530 nm to 535 nm. The quick reduction of the intensity of the absorption peak means that metal gold nanoparticles (Au NPs) are leached by the hydrochloric acid. If the concentration of the hydrochloric acid is increased, the intensity reduction of the absorption peak is further exacerbated.

Figure 5B:
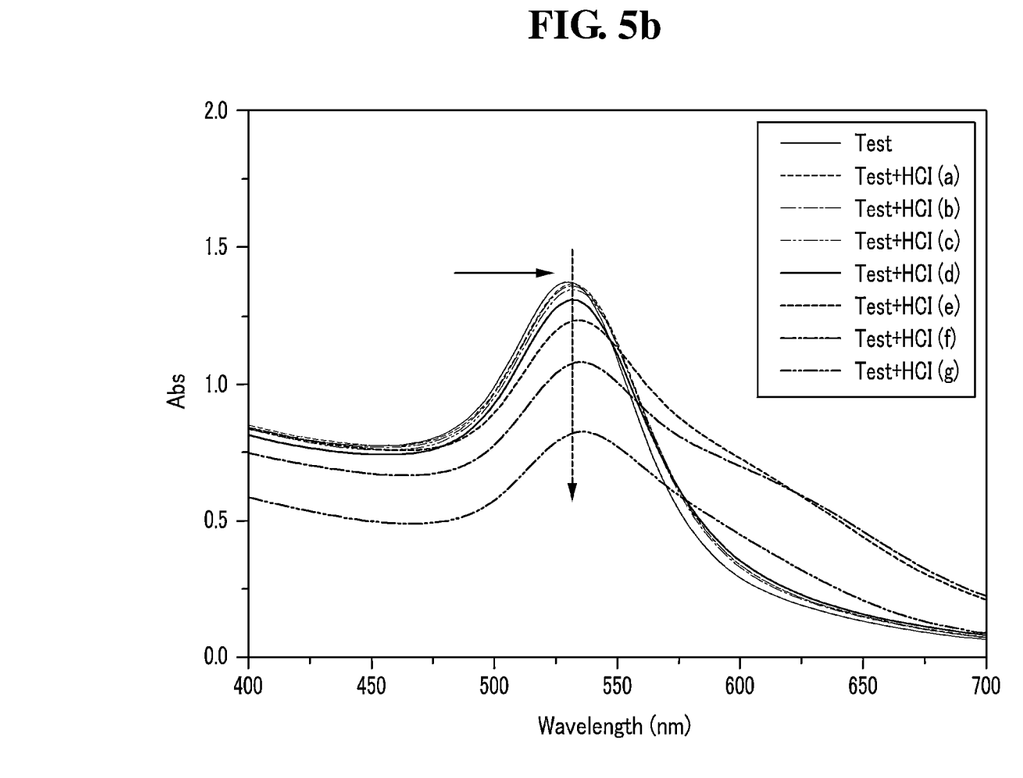
FIG. 5b is a view showing an ultraviolet ray-visible ray absorption spectrum of an gold nanoparticle aqueous dispersion using hydrogen peroxide as an oxidizing agent in an environment including hydrochloric acid of different concentrations.

FIG. 5b is a view showing an ultraviolet ray-visible ray absorption spectrum of a gold nanoparticle aqueous dispersion using hydrogen peroxide as an oxidizing agent in an environment including hydrochloric acid of different concentrations. The hydrochloric acid concentration of each graph is (a) 100 ppm, (b) 200 ppm, (c) 500 ppm, (d) 1,000 ppm, (e) 2,000 ppm, and (f) 5,000 ppm.

A similar result to the case of using the nitric acid as the oxidizing agent is obtained in the case of using the hydrogen peroxide as the oxidizing agent. However, when using the hydrogen peroxide, the degree of the SP reduction (surface plasmon damping) is smaller than the case of using the nitric acid, and has the red shift into 540 nm.

Figure 6A:
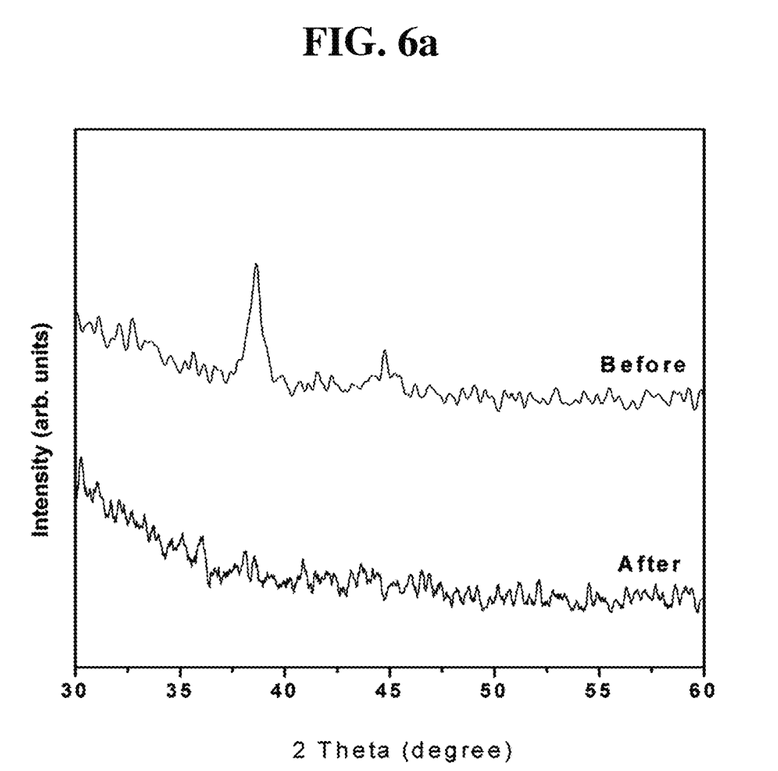
FIG. 6a is a graph of an XRD pattern for gold nanoparticles before and after mixing hydrochloric acid.

FIG. 6a is a graph of an XRD pattern for a gold nanoparticles (Au NPs) before and after mixing hydrochloric acid.

To clearly comprehend the detection mechanism, a change of a structure generated during the detection reaction may be confirmed through Xray diffraction analysis (XRD). As shown in FIG. 6a, the gold nanoparticles (Au NPs) without the reaction has a significant peak at 2θ=37.8 corresponding to the 111 peak of the gold metal having a face-centered cubic structure. It may be confirmed that the mean crystallite diameter of the nanoparticles is 27 nm from Scherrer's formula. As shown in FIG. 6a, the XRD pattern of the gold nanoparticle (Au NP) sample is quickly changed after the detection reaction. A fact that the peak corresponding to the metallic gold disappears means the metal is dissolved when the hydrochloric acid and the strong oxidizing agent exist.

Figure 6B:
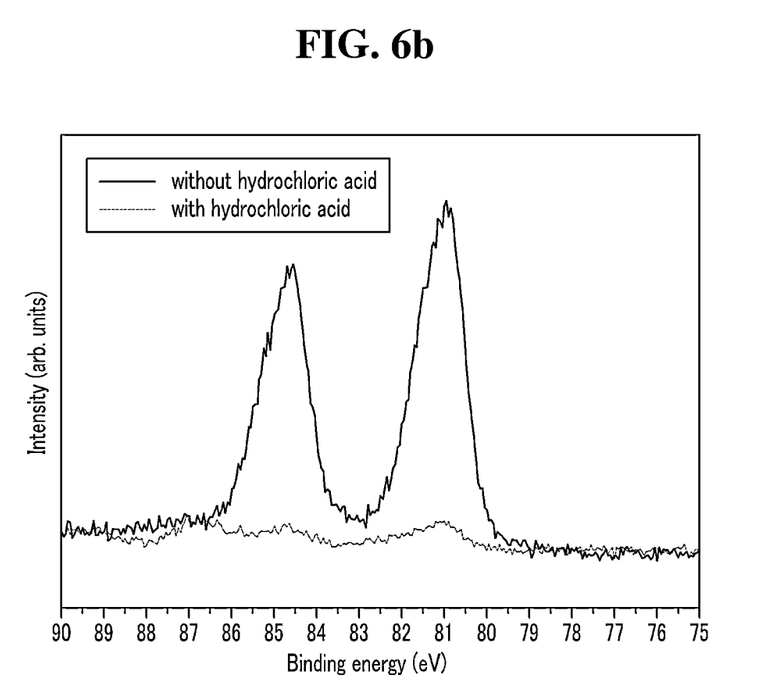
FIG. 6b is a graph of an XRD spectrum for gold nanoparticles before and after mixing hydrochloric acid.

FIG. 6b is a graph of an XRD spectrum for gold nanoparticles (Au NPs) before and after mixing hydrochloric acid.

To comprehend a possible interreaction between the hydrochloric acid and the gold nanoparticles (Au NPs), Xray photoelectron spectroscopy may be performed. Referring to FIG. 6b, for the pure gold nanoparticles (Au NPs), the gold 4f7/2 spectrum may be divided into two peaks respectively having the center at 81.0 eV and 84.5 eV, and two peaks corresponds to a binding energy of Au(0) and Au(I). In contrast, if the hydrochloric acid at 5000 ppm is added to the environment including the nitric acid, the intensity of the two peaks is quickly reduced and the center of the peaks is shifted to 81.2 eV and 86.5 eV, and this means that the hydrochloric acid oxidizes the gold nanoparticles in the environment including the strong oxidizing agent.

Figure 7:
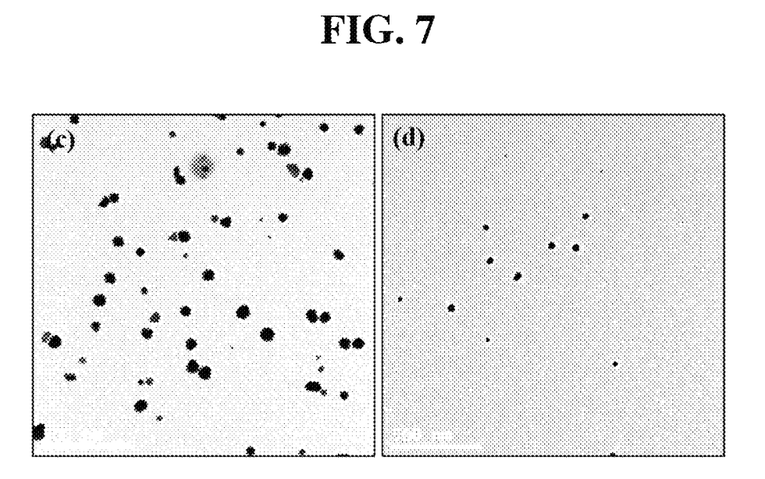
FIG. 7 is a view comparing a TEM image of gold nanoparticles in a case (c) of mixing hydrochloric acid and a case (d) not including hydrochloric acid.

FIG. 7 is a view comparing a transmission electron microscopy (TEM) image of gold nanoparticles in a case (c) of mixing hydrochloric acid and a case (d) of not including hydrochloric acid. The shape change generated during the detection reaction may be confirmed through the TEM image.

Referring to (c) and (d) of FIG. 7, a clear image of the gold nanoparticles of a spherical shape having the crystallite diameter of the range of 25 to 35 nm may be observed before adding the hydrochloric acid. However, after adding the hydrochloric acid, the size and the density of the nanoparticles is decreased.

EXPERIMENTAL EXAMPLE

A colorimetric test for the hydrochloric acid recognition is performed at room temperature under atmospheric pressure. The detection process is as follows.

That is, 200 μl of a gold nanoparticle (Au NP) dispersion solution is obtained and is diluted along with 1 ml of deionized water in a 5 ml glass bottle. Also, the oxidizing agent (nitric acid or hydrogen peroxide) of a predetermined amount is added to the dispersion solution. The sample as prepared above is stored for 30 minutes and then the ultraviolet ray-visible ray spectrum is measured such that it is confirmed that the addition of the oxidizing agent does not influence the SP spectrum.

Also, a sample of 1 ml of each of other inorganic acids and salts is added to the glass bottle including the gold nanoparticle (Au NP) dispersion solution, and the glass bottle is shaken and left 30 minutes.

Then, the color change is firstly confirmed by the naked eye, and is confirmed by an ultraviolet ray-visible ray spectroscope.

Figure 8A:
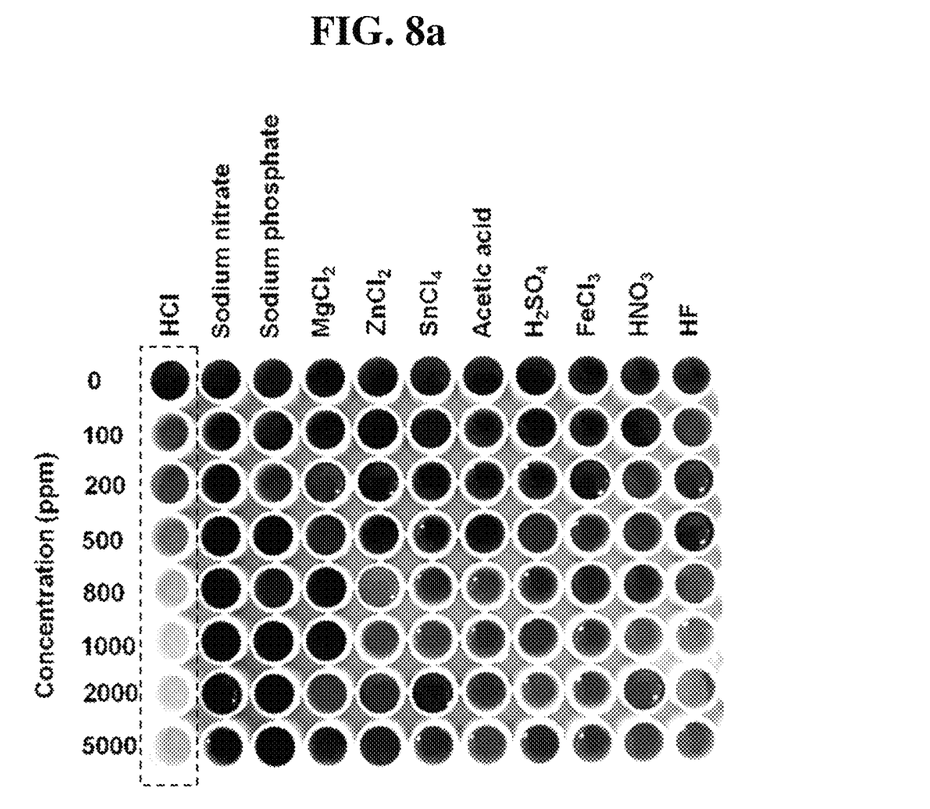
FIG. 8a is a picture comparing effects in a case of adding hydrochloric acid to a gold nanoparticle aqueous dispersion and a case of adding an interfered chemical material in an environment including nitric acid.

FIG. 8a is a picture comparing effects in a case of adding hydrochloric acid to a gold nanoparticle dispersion solution and a case of adding an interfered chemical material to an environment including nitric acid. A visual color change of the gold nanoparticle dispersion solution may be confirmed.

A heavy pink of the gold nanoparticle dispersion solution is gradually changed as the concentration of the hydrochloric acid is increased. The color change speed is increased according to the increasing of the concentration of the hydrochloric acid. For hydrochloric acid of a sufficient amount (more than 2,000 ppm), the mixture solution is changed to colorlessness within 15 to 20 minutes. In the environment in which another inorganic acid and common salt exist, the red color of the gold nanoparticle dispersion solution is not affected.

However, there are chemical materials of several kinds shifting the color, if hydrofluoric acid (HF acid) is added, the color of the mixture solution is shifted from a pinkish red to a light purple. Similarly, $FeCl_3$ also slightly causes the color change. This is because $Fe^{3+}$ ions have a yellow color in the water environment.

However, other chemical species checked in the present experiment do not generate the remarkable color change caused by the hydrochloric acid.

Figure 8B:
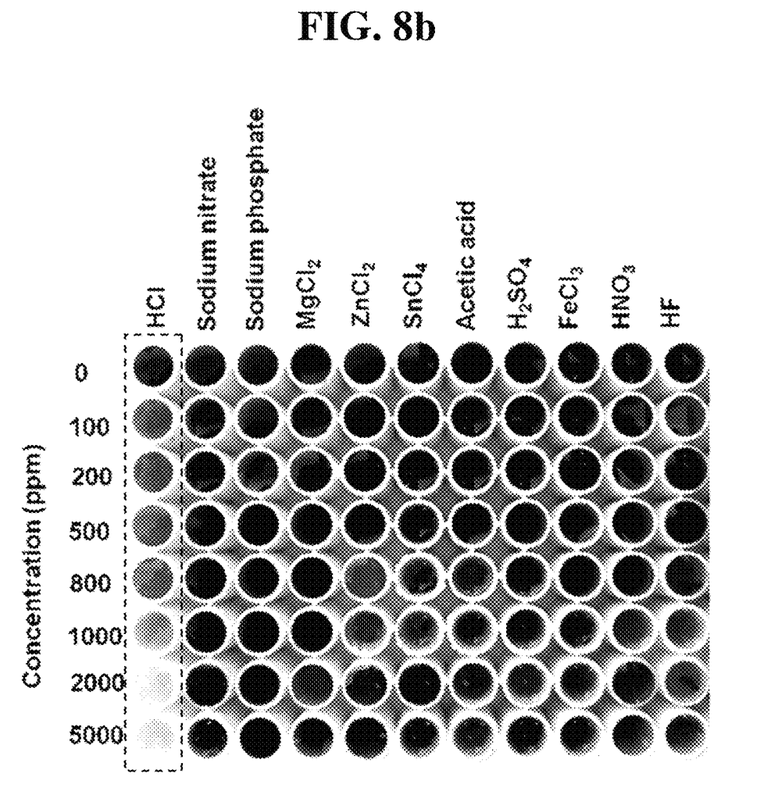
FIG. 8b is a picture comparing effects in a case of adding hydrochloric acid to a gold nanoparticle aqueous dispersion and a case of adding an interfered chemical material in an environment including hydrogen peroxide.

FIG. 8b is a picture comparing effects in a case of adding hydrochloric acid to a gold nanoparticle dispersion solution and a case of adding an interfering chemical material in an environment including hydrogen peroxide. In the case of using hydrogen peroxide instead of the nitric acid, the similar color change may be observed.

However, in this case, the degree of the color change is weak and the time becomes longer. In the environment, when the amount of hydrochloric acid is small, the color change may be slower.

One of drawbacks of a conventional hydrochloric acid detector is a difficulty in identifying a source of chloride ions. Also, most optical chromic sensors are easily disturbed by other salts or ions (mostly negative ions).

To confirm whether the system of the present invention has specificity for hydrochloric acid, the absorption reaction of the system of the present invention is measured through eight acids, the common salts, and the negative ions (sulfuric acid, fluorine acid, acetic acid, zinc chloride, tin chloride, sodium chloride, iron chloride (III), phosphate, chlorate, and nitric acid).

Figure 9A:
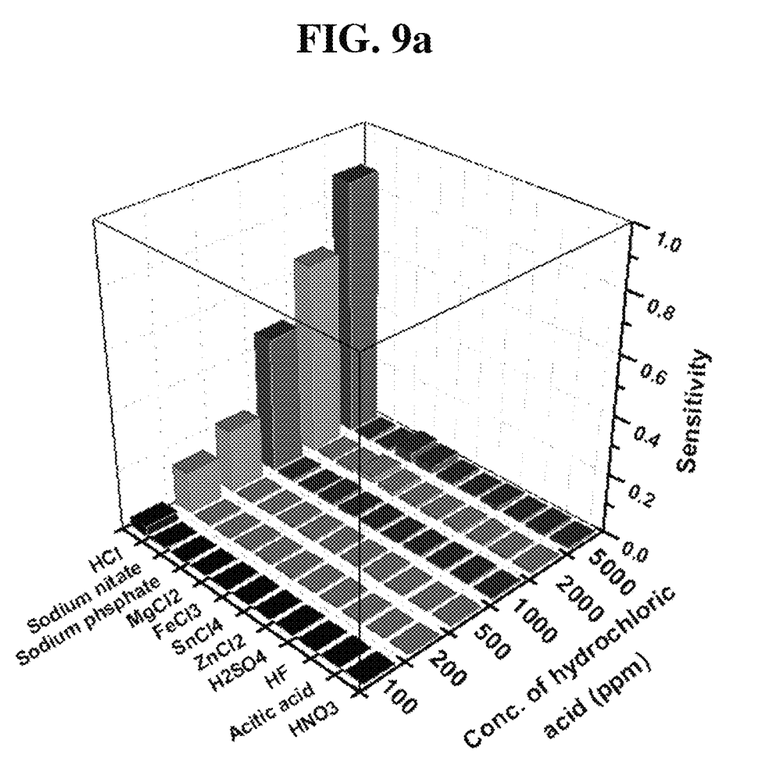
FIG. 9a is a graph comparing an influence according to addition of hydrochloric acid with different concentrations and a chemical material of different kinds that frequently meets a gold nanoparticle aqueous dispersion for a relative reduction of an SP spectrum.

FIG. 9a is a graph comparing an influence according to an addition of hydrochloric acid with different concentrations and a chemical material of different kinds that frequently meets a gold nanoparticle dispersion solution for a relative reduction of an SP spectrum.

As shown in FIG. 9a, the existence of other common ions and the salt may be cause the color change of the gold nanoparticle dispersion solution. Only hydrochloric acid may generate the remarkable reduction in the absorption spectrum, and no significant color change is observed with the other chemical materials.

Meanwhile, to determine whether the gold nanoparticle basic sensor can be applied to a general natural system, an actual water sample including underground water, tap water, river water, and sea water is collected and analyzed by the hydrochloric acid detection system according to the present invention.

Figure 9B:
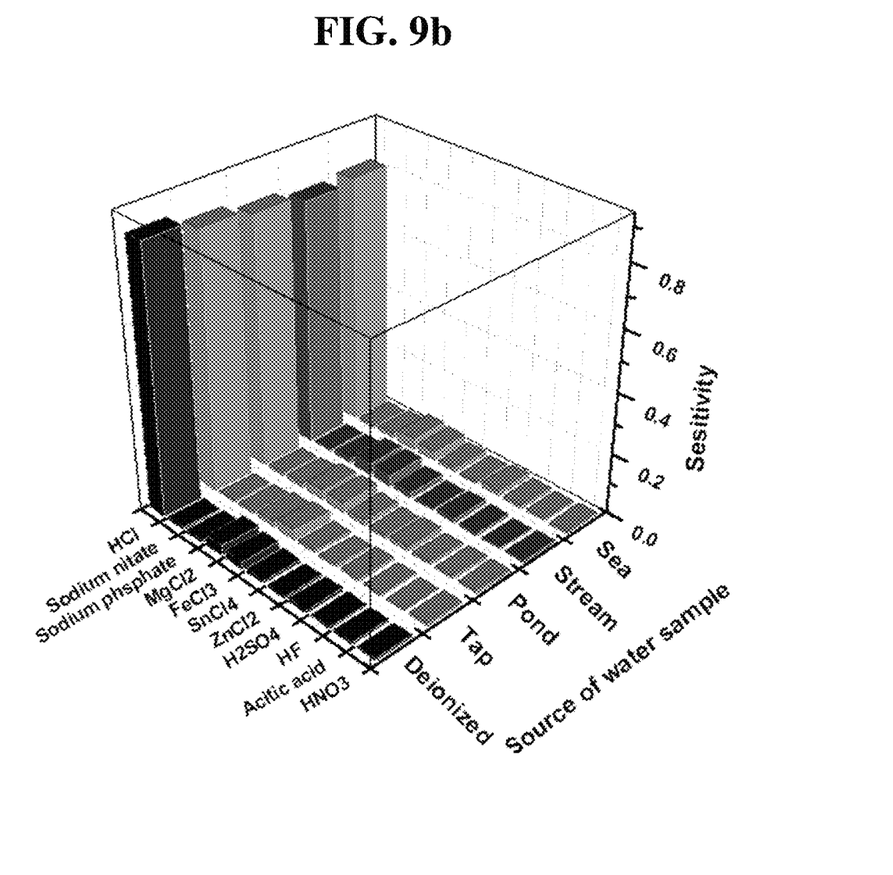
FIG. 9b is a graph comparing an influence according to addition of hydrochloric acid with different concentrations and a chemical material of different kinds that frequently meets a gold nanoparticle aqueous dispersion in various water qualities for a relative reduction of an SP spectrum.

FIG. 9b is a graph comparing an influence according to an addition of hydrochloric acid with different concentrations and a chemical material of different kinds that frequently meets a gold nanoparticle dispersion solution in various water qualities for a relative reduction of an SP spectrum.

As the experimental results, the detection system according to an exemplary embodiment of the present invention never meaningfully reacts with the water sample, and accordingly, similar to the deionized water, the actual water sample hardly disturbs the performance of the detection system of the present invention.

In summary, the present invention relates to a selective recognition technique of hydrochloric acid in a water environment based on hydrochloric acid dissolution caused by an absorption reduction of gold nanoparticles. The process according to an exemplary embodiment of the present invention does not use any leveling agent such that the process is simple and easy to use.

This process has high separation sensitivity from common salts, and negative ions may be directly used in a natural number system. Through these characteristics, the system according to the present invention may be a possible means for testing hydrochloric acid in a sea ecosystem that is easily exposed to industrial pollution.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A detection method using colorimetric analysis, comprising: providing a first solution of metal nanoparticles and an oxidizing agent; providing a second solution including chloride ions; mixing the first solution and the second solution into a mixture solution; testing and measuring a red shift and an intensity decrease of ultraviolet ray-visible ray absorption peak of the mixture solution as compared to the first solution to determine a concentration of the chloride ions, wherein the red shift occurs by a leaching of the metal nanoparticles.

2. The detection method of claim 1, wherein
the first solution is provided as a detection solution and the second solution is provided as a detection target
wherein the detection solution is mixed with the detection target to test for and measure a red shift and an intensity decrease of ultraviolet ray-visible ray absorption peak to determine a concentration of the chloride ions of the detection target.

3. The detection method of claim 2, wherein
the detection target includes at least one among sea water, stream water, pond water, tap water, and deionized water including the chloride ions.

4. The detection method of claim 2, wherein the detection target including the chloride ions is hydrochloric acid.

5. The detection method of claim 1, wherein the diameter of the metal nanoparticles is in a range of 10 to 100 nm.

6. The detection method of claim 5, wherein the diameter of the metal nanoparticles is in a range of 20 to 30 nm.

7. The detection method of claim 1, wherein the metal nanoparticles include at least one of gold (Au) nanoparticles and silver (Ag) nanoparticles.

8. The detection method of claim 1, wherein the oxidizing agent includes at least one of nitric acid ($HNO_3$) and hydrogen peroxide ($H_2O_2$).

9. The detection method of claim 2 wherein
in the testing and measuring of the red shift and an intensity decrease of an ultraviolet ray-visible ray absorption peak of the mixture solution,
after the detection solution and the detection target are mixed and left for a predetermined time, the red shift and an intensity decrease of the ultraviolet ray-visible ray absorption peak is tested and measured by comparing with the detection target before the mixing.

* * * * *

UNITED STATES PATENT AND TRADEMARK OFFICE
CERTIFICATE OF CORRECTION

PATENT NO. : 9,128,074 B2  
APPLICATION NO. : 13/581850  
DATED : September 8, 2015  
INVENTOR(S) : Chang Soo Han et al.

Page 1 of 1

It is certified that error appears in the above-identified patent and that said Letters Patent is hereby corrected as shown below:

On The Title Page, Item (73)

Replace

Assignee: Korea Institute Of Machinery & Materials  
                Daejeon, Korea with         Assignee: Intellectual Discovery Co., Ltd.  
                Seoul, Korea Signed and Sealed this  
Fifteenth Day of December, 2015

Michelle K. Lee  
*Director of the United States Patent and Trademark Office*